United States Patent [19]
Kalvinsh et al.

[11] Patent Number: 5,859,056
[45] Date of Patent: Jan. 12, 1999

[54] PHARMACEUTICAL COMPOSITION FOR TREATING CARDIOVASCULAR DISEASES CONTAINING 3-(2,2,2-TRIMETHYLHYDRAZINIUM)PROPIONATE AND γ-BUTYROBETAINE

[76] Inventors: Ivars Kalvinsh, Apartment 8, Miera 17, LV-2169 Salaspils; Maris Veveris, Apartment 20, Vejavas 10/2, LV-1035 Riga, both of Latvia

[21] Appl. No.: 11,380

[22] PCT Filed: Aug. 20, 1996

[86] PCT No.: PCT/LV96/00002

§ 371 Date: Feb. 19, 1998

§ 102(e) Date: Feb. 19, 1998

[87] PCT Pub. No.: WO97/06794

PCT Pub. Date: Feb. 27, 1997

[30] Foreign Application Priority Data

Aug. 21, 1995 [LV] Latvia .................................. P-95-256

[51] Int. Cl.$^6$ ........................ A61K 31/205; A61K 31/195
[52] U.S. Cl. ........................................... 514/556; 514/565
[58] Field of Search ....................................... 514/556, 565

[56] References Cited

U.S. PATENT DOCUMENTS 4,451,485  5/1984  Kalvinsh .................................. 424/316

FOREIGN PATENT DOCUMENTS 2105992  4/1983  United Kingdom .

OTHER PUBLICATIONS

Simkhovich, B Z et al.; Biochem. Pharmacol. vol. 37, No. 2, 1988, pp. 195–202.

W. Rotzsch et al, Acta biol. med. germ., 1959, Band 3, pp. 28–36.

Hosein E.A. et al, Nature, 1960, vol. 187, pp. 321–322.

Hosein E.A. et al, Nature, 1959, vol. 183, pp. 328–329.

Burgen A.S.V. et al, Brit. J. Pharmacol., 1949, 4, pp. 229–233.

Simkhovich, B Z et al, Vopr. Med. khim. vol. 32, No. 4, 1986, pp. 72–75.

Chemical Abstracts, vol. 105, 15, Nr. 127077, 13 Oct. 86, pp. 45–46.

*Primary Examiner*—Phyllis G. Spicack
*Attorney, Agent, or Firm*—Colin P. Abrahams

[57] ABSTRACT

A pharmaceutical composition containing 3-(2,2,2-trimethylhydrazinium)propionate and γ-butyrobetaine with a pharmaceutically acceptable carrier for the treatment of cardiovascular diseases is disclosed. The composition may be for oral, parenteral, subcutaneous or rectal administration and exhibits low toxicity and a wide interval of therapeutic action safety.

11 Claims, No Drawings

PHARMACEUTICAL COMPOSITION FOR TREATING CARDIOVASCULAR DISEASES CONTAINING 3-(2,2,2-TRIMETHYLHYDRAZINIUM)PROPIONATE AND γ-BUTYROBETAINE

The invention relates to pharmaceutical compositions, namely, to pharmaceutical compositions for the treatment of such heart and blood vessel diseases, which are connected with blood circulation disturbances of various genesis and localization, stenocardia, myocardium infarction, arrhythmias, hypertension, myocarditis as well as low heart potency.

The proposed therapeutic composition contains known chemical substances, the use of which gives unexpected pharmacological effects. Namely, there is offered a pharmaceutical composition which contains γ-butyrobetaine in a combination with 3-(2,2,2-trimethyl-hydrazinium) propionate as an active system and pharmaceutically acceptable fillers or solvents.

In the treatment of cardiovascular diseases, 3-(2,2,2-trimethyl-hydrazinium)propionate is a known preparation (Mildronate, Quaterine) (UK patent GB 2105992), the mechanism of action of which is based on the limitation of carnitine biosynthesis rate and the related long-chain fatty acid Transport limitation through mitochondria membranes (Simkhovich B. Z., Shutenko Z. V., Meirena D. V. et al. 3-(2,2,2-trimethylhydrazinium)-propionate (THP)—a novel γ-butyrobetaine hydroxylase inhibitor with cardioprotective properties. Biochem.Pharmacol. 1988, 37, 195–202).

BACKGROUND ART

γ-Butyrobetaine (actinine), from which the mammalian organism synthesises carnitine, was primarily characterised as a toxic substance which accelerates respiration, causes salivation and lacrimation, pupil dilation, vasoconstriction and heart stop in diastole (W. Linneweh, Z. Physiol. Chem., 42, 181, 1929). At the same time, in later papers other authors ascertained that γ-butyrobetaine is extremely low toxic ($LD_{50}$>7000 mg/kg, s.c.). (W. Rotzsch, I. Lorenz, E. Strack, Acta biol. med. ger. 1959,3,28–36).

In the literature data on nonsubstituted γ-butyrobetaine cardiovascular effects are missing, though it was reported (Hosein E. A., McLennan H. Pharmacological action of γ-butyrobetaine. Nature, 1959, 183, 328–329) that γ-butyrobetaine is a substance similar to acetyl choline with a prolonged action. However, later the same authors reported that by an error the experiments involved, instead of γ-butyrobetaine, its methyl ester which in fact possesses cholinergic properties. Contrary to the former nonesterified γ-butyrobetaine was characterised as a pharmacologically inert substance (E. A. Hosein, P. Proulx, Isolation and probable functions of betaine esters in brain metabolism, Nature, 1960, 187, 321–322. A. S. V. Burgen, F. Hobiger. Brit. J. Pharmacol., 4, 229 (1949), E. Strack, K. Foesterling. Z. Physiol. Chem., 1953, 295, 377).

γ-Butyrobetaine administration increases the level of carnitine biosynthesis in the organism serving as a substrate in this process. Thus, it would be natural to anticipate that in the organism at a simultaneous administration of camitine biosynthesis blocker 3-(2,2,2-trimethyl-hydrazinium) propionate and γ-butyrobetaine, the pharmacological effect of 3-(2,2,2-trimethylhydrazinium)propionate should decrease because carnitine biosynthesis is activated if γ-butyrobetaine concentration increases. On the contrary, it was now unexpectedly discovered that the opposite effect is observed, i.e. γ-butyrobetaine intensifies the effect of 3-(2,2,2-trimethylhydrazinium)propionate on the cardiovascular system.

DISCLOSURE OF THE INVENTION

The experiments were performed on male and female (2.9–3.8 kg) anaesthetized cats (urethane 200 mg/kg and chloralose 50 mg/kg, both i.p.).

The chest was opened in the experimental animals, which were artificially respirated, and blood pressure in the carotid artery as well as general aorta blood flow were measured on physiograph DMP-46 "Narco Bio-Systems" USA.

It was detected that the pharmaceutical composition which contains γ-butyrobetaine in combination with 3-(2,2,2-trimethylhydrazinium)-propionate possesses a marked effect on blood vessel tonus and blood circulation, which exceeds every separate active substance action, blood pressure decrease is not practically observed, while the total blood flow increases very considerably (Table 1).

TABLE 1

3-(2,2,2-Trimethylhydrazinium)propionate (M), γ-butyrobetaine (GBB), acetyl choline (Ach) and the pharmaceutical composition effects on hemodynamics of anesthetised cats

| Substance | Dose, i.v. mg/kg | Blood pressure changes, % | Heart rate changes | Blood flow rate changes, % |
|---|---|---|---|---|
| M | 5.0 | ±3 | ±3 | +5 |
|   | 10.0 | ±5 | ±3 | +8*) |
| GBB | 5.0 | ±+4 | ±5 | 6 |
|   | 10.0 | −7÷+3 | ±5 | 12*) |
| M + GBB | 5.0 + 5.0 | −7÷+3 | ±5 | +18*)**) |
| Ach | 0.001 | −35*)**) | −20*)**) | ±8 |

*)$p<0.05$ in comparison with the initial data
**)$p<0.05$ in comparison with GBB and M groups If this effect was connected with an earlier, incorrectly postulated cholinergic component, which mainly relates to γ-butyrobetaine ester (The Merck Index, Eleventh Edition, 1871) impurities in the samples of insufficiently purified γ-butyrobetaine, then one would anticipate a significant decrease in the blood pressure. On the contrary, such a cardiovascular effect indicates a positive inotropic effect of the present therapeutic composition with simultaneous decrease in peripheral resistance according to an absolutely different mechanism, which can be applied in the treatment of low heart potency and blood circulation failures of various genesis.

The pharmaceutical composition containing γ-butyrobetaine also, by 2–3 times, more potently affects adrenaline-induced blood vessel spasms in isolated rabbit ear than the known preparation 3-(2,2,2-trimethylhydrazinium)propionate (Table 2).

TABLE 2

3-(2,2,2-Trimethylhydrazinium)propionate (M) and γ-butyrobetaine (GBB) effects on adrenaline-induced isolated rabbit ear blood vessel spasms

| Substance, concentrat. | Perfusion pressure (mm Hg) max/min | | | | Perfusion pressure decrease |
|---|---|---|---|---|---|
| | Initial parameters | | Final data (after adrenaline 3.10$^{-7}$ M addition) | | |
| ($\mu$M) | max | min | max | min | (%) |
| M.0.3 | 38 ± 5 | 8 ± 2 | 125 | 80 | 1 |
| M.1.0 | 38 ± 5 | 8 ± 2 | 123 | 77 | 4 |
| M.2.0 | 38 ± 5 | 8 ± 2 | 126 | 80 | 8* |
| GBB,0.3 | 38 ± 5 | 8 ± 2 | 124 | 76 | 6 |
| GBB,1.0 | 38 ± 5 | 8 ± 2 | 125 | 80 | 15*) |
| GBB,2.0 | 38 ± 5 | 8 ± 2 | 125 | 78 | 18**) |
| M + GBB, (1.0 + 1.0) | 38 ± 5 | 8 ± 2 | 125 | 78 | 22**) |
| M + GBB, (2.0 + 2.0) | 38 ± 5 | 8 ± 2 | 126 | 80 | 33**)***) |

*)p<0.05 against the control
**)p<0.01 against the control
***)p<0.05 against GBB and M groups In the same way it unexpectedly turned out that both substances combined in one pharmaceutical composition act synergically causing a further spasmolytic effect intensification.

Moreover, it unexpectedly was discovered that the basis of this vasodilating effect is NO-synthase activation, which cannot be completely blocked even by L-NO$_2$-arginine if a composition of 3-(2,2,2-trimethylhydrazinium)propionate and γ-butyrobetaine is used (Table 3*).

TABLE 3

3-(2,2,2-Trimethylhydrazinium)propionate (M) and γ-butyrobetaine (GBB) and their pharmaceutical combination effects on adrenaline-induced rabbit ear blood vessel spasm in the presence of L-nitro-arginine (L-NO$_2$-Arg) (10mg/l)

| Substance concentrat. | Perfusion pressure (mm Hg) max/min | | | | Perfusion pressure decrease |
|---|---|---|---|---|---|
| | Initial parameters | | Final data (after adrenaline 3.10$^{-7}$ M and L-NO$_2$ Arg addition) | | |
| ($\mu$M) | max | min | max | min | (%) |
| M,0.3 | 36 ± 5 | 7 ± 2 | 165 | 102 | 0 |
| M,1.0 | 36 ± 5 | 7 ± 2 | 163 | 100 | 0 |
| M,2.0 | 36 ± 5 | 7 ± 2 | 165 | 100 | 2 |
| GBB, 0.3 | 35 ± 5 | 8 ± 2 | 168 | 105 | 0 |
| GBB. 1.0 | 35 ± 5 | 8 ± 2 | 165 | 100 | 0 |
| GBB, 2.0 | 35 ± 5 | 8 ± 2 | 163 | 100 | 0 |
| M + GBB, (1.0 + 1.0) | 35 ± 5 | 8 ± 2 | 165 | 100 | 3 |
| M + GBB, (2.0 + 2.0) | 35 ± 5 | 8 ± 2 | 163 | 98 | 6*) |

*)p<0.05

Special experiments showed that the pharmaceutical composition on the basis of γ-butyrobetaine possesses also antiarrhythmic properties. Thus, in CaCl$_2$-induced arrhythmias in mice the pharmaceutical composition containing 50 and 100 mg/kg of γ-butyrobetaine demonstrated a statistically significant protection from lethal arrhythmia (in 30–40% cases). This experiment was performed on male and female conscious albino mice (19–26 g) administering to their tail vein a 2% (by weight) calcium chloride solution, animal protection against lethal arrhythmia being used as an effect criterion (Table 4).

TABLE 4

3-(2,2,2-Trimethylhydrazinium)propionate (M), γ-butyrobetaine (GBB) and their combination effect on CaCl$_2$-induced lethal arrhythmias in mice

| Substance | Dose, mg/kg, p.o. | The number of observations | Survive | Protection % against the control |
|---|---|---|---|---|
| M | 8 | 10 | 2 | 10 |
| | 20 | 10 | 3 | 20 |
| | 30 | 10 | 4 | 30* |
| | 50 | 10 | 4 | 30* |
| | 100 | 10 | 5 | 40 |
| GBB | 8 | 10 | 2 | 10 |
| | 20 | 10 | 1 | 0 |
| | 30 | 10 | 3 | 20 |
| | 50 | 10 | 5 | 40* |
| | 100 | 10 | 4 | 30* |
| M + GBB | 42 + 8 | 10 | 2 | 10 |
| | 33 + 16.5 | 10 | 6 | 50* |
| | 30 + 20 | 10 | 5 | 40* |
| | 25 + 25 | 10 | 6 | 50* |
| | 20 + 30 | 10 | 7 | 60* |
| | 16.5 + 33 | 10 | 7 | 60* |
| | 10 + 40 | 10 | 3 | 20 |
| | 50 + 50 | 10 | 6 | 50* |
| | 40 + 60 | 10 | 8 | 70* |
| | 33 + 67 | 10 | 4 | 30* |
| Control | — | 10 | 1 | 0 |
| Quinidine | 10 | 10 | 2 | 10 |
| | 30 | 10 | 4* | 30* |
| | 50 | 10 | 6* | 50* |
| Etmozine | 5 | 10 | 3 | 20 |
| | 10 | 10 | 5* | 40* |
| | 30 | 10 | 5* | 40* |

*p<0.05 against the control

γ-Butyrobetaine's closest structural analog, 3-(2,2,2-trimethyl-hydrazinium)propionate, also possesses, as known, (UK patent GB 2105992) a similar antiarrhythmic efficacy. It was now discovered that the effect of both substances in a combination in the form of a pharmaceutical composition is higher than each substance has separately (Table 4), exceeding that of the known antiarrhythmic agents Quinidine and Etmozine. The very low toxicity of the combination claimed compared with the control preparations should also be noted.

Acute toxicity was studied on male and female albino mice (19–26 g), 10 animals in a group. The substances were administered as a 10% solution orally or i.v. (with 0.004 ml/sec rate). It was determined that for γ-butyrobetaine at oral administration LD$_{50}$>4500 mg/kg, but at intravenous injection LD$_{50}$=1860 (1430–2418) mg/kg, which testifies that γ-butyrobetaine is a practically nontoxic agent.

At oral administration of a mixture of γ-butyrobetaine and 3-(2,2,2-trimethylhydrazinium)propionate (1:1 by weight) its LD$_{50}$>4500 mg/kg, and at i.v. injection LD$_{50}$=1750 (1434–2135) mg/kg. So, being used in a combination, the toxicity of both substances has no synergic character.

Similar to mice, also in rats, applying a pharmaceutical composition containing 3-(2,2,2-trimethylhydrazinium) propionate and γ-butyrobetaine, in CaCl$_2$-induced arrhythmias there is observed a marked combination protective effect against lethal CaCl$_2$-induced arrhythmias (Table 5).

TABLE 5

3-(2,2,2-Trimethylhydrazinium)propionate (M), γ-butyrobetaine (GBB) and their combination effect on CaCl$_2$-induced lethal arrhythmias in rats

| Substance | Dose, mg/kg, p.o. | The number of observations | Survive | Protection % against the control |
|---|---|---|---|---|
| M | 10 | 5 | 1(20%) | 15 |
|  | 20 | 5 | 1(20%) | 23 |
|  | 30 | 5 | 1(20%) | 25 |
| GBB | 10 | 5 | 1(20%) | 20 |
|  | 30 | 5 | 1(20%) | 32 |
| M + GBB | 30 + 10 | 5 | 2(40%) | 37 |
|  | 30 + 20 | 5 | 1(20%) | 35 |
|  | 30 + 30 | 5 | 4(80%) | 60* |
|  | 20 + 30 | 5 | 3(60%) | 52* |
| Control | — | 5 | 0 | 0 |
| Quinidine | 10 | 5 | 2(40%) | 46 |
|  | 3 | 5 | 1(20%) | 25 |
| Etmozine | 3 | 5 | 1(10%) | 20 |
|  | 10 | 5 | 2(40%) | 46* |

*p < 0.05 against the control

These experiments were performed on male and female albino rats (190 to 230 g) anesthetized with urethane (I1200 mg/kg, i.p.), and after 2% calcium chloride solution administration to animal foot vein ECG was registered in II standard lead.

In order to test the 3-(2,2,2-trimethylhydraziniur) propionate-and γ-butyrobetaine-containing pharmaceutical composition's usefulness in the prophylaxis and/or treatment of myocardium infarction, we examined how effectively it protects myocardium from ischemia- and reperfusion-induced rhythm disturbances and heart stop because the literature cites γ-butyrobetaine to cause heart stop in diastole (W. Linneweh, Z. Physiol. Chem..42, 181, 1929).

TABLE 6

3-(2,2,2-Trimethylhydrazinium)propionate (M), γ-butyrobetaine (GBB) and their combination effect on ischemia- and reperfusion-induced heart rhythm disturbances in rats in the therapeutic regimen

| Substance | Total dose, mg/kg | Rhythm disturbances (the number of animals from total numb) | | | ST rise during occlusion (mV) |
|---|---|---|---|---|---|
|  |  | Ventricular tachycardy | Ventricular fibrillation | Lethality |  |
| M | 50 (25 -injection + 25 -infusion) | 10/10 | 8/10 | 3/10 | 0.4 ± 0.1 |
| GBB | 50 (25 -injection + 25 -infusion) | 7/10 | 4/10* | 1/10* | 0.23 ± 0.05* |
| M + GBB | 50 + 50 (25 + 25 - injection and 25 + 25 - infusion) | 8/10 | 5/10* | 0/10* | 0.20 ± 0.04 |
| Control |  | 15/15 | 15/15 | 7/15 | 0.44 ± 0.08 | p<0.05

The experiments were carried out on Wistar rats (260–330 g). During phenobarbital anesthesia (50 mg/kg, i.p.) and artificial respiration their chest was opened and the left coronary artery was ligated with 6.0 Silk Ethicon thread which was pulled out through plastic pipe. Occlusion was made by pressing the plastic pipe to the heart surface, and ischaemia stage was controlled by ECG, fixing ischaemia-induced changes in ECG. Solutions of the substances or saline were i.v. injected in two regimens:

1) prophylactically—30 min before occlusion by administration of 50 mg/kg,
2) therapeutically—1.5 min after occlusion by administering 25 mg/kg in injection and 25 mg/kg infusively. Infusion was stopped 2 min after reperfusion.

The experiments exhibited that γ-butyrobetaine in the therapeutically regimen during infusion effectively protects myocardium from ischaemia-reperfusion-induced myocardium damages and ventricular fibrillations which are partially resumed after infusion termination (Table 6). On the contrary, γ-butyrobetaine is ineffective in the prophylactic regimen (Table 7).

TABLE 7

3-(2,2,2-Trimethylhydrazinium)propionate (M), γ-butyrobetaine (GBB) and their combination effect on ischemia and reperfusion-induced heart rhythm disturbances in rats in the prophylactic regimen

| Substance | Total dose, mg/kg | Rhythm disturbances (the number of animals from total numb) | | | ST rise during occlusion (mV) |
|---|---|---|---|---|---|
|  |  | Ventricular tachycardy | Ventricular fibrillation | Lethality |  |
| M | 50 (proph.) | 7/8 | 5/8 | 2/8 | 0.31* |
| GBB | 50 (proph.) | 8/8 | 6/8 | 3/8 | 0.36 |
| M + GBB | 50 + 50 (proph.) | 7/10 | 5/10* | 1/10* | 0.27* |
| Control |  | 15/15 | 15/15 | 7/15 | 0.44 |

* p<0.05

The efficacy of 3-(2,2,2-trimethylhydrazinium)propionate in the therapeutic regimen on this model is relatively low (Table 6). Its action is markedly better in the case of prophylaxis, i.e., 30 min. before occlusion when it protects myocardium from ischemia increase during occlusion (Table 7).

On the other hand, the 3-(2,2,2-trimethylhydrazinium) propionate and γ-butyrobetaine-containing pharmaceutical composition effectively protects myocardium from ischemia-reperfusion-induced rhythm disturbances both in the prophylactic and therapeutic regimens (Tables 6 and 7).

Thus, it was discovered that the pharmaceutical composition containing 3-(2,2,2-trimethylhydrazinium)propionate and γ-butyrobetaine in combination possesses a wide spectrum of cardiovascular action which is connected with its effect on blood vessel and myocardium tonus, blood flow as well as cardiac rhythm including myocardium infarction.

Hence, the pharmaceutical composition containing 3-(2,2,2-trimethyl-hydrazinium)propionate and γ-butyrobetaine is promising for the treatment of heart-blood vessel diseases, the efficacy of which is higher compared to each separate substance.

It is preferred that the ratio of 3-(2,2,2-trimethylhydrazinium)-propionate to γ-butyrobetaine in the composition is within 1:10, preferably, 1:3, to 3:1.

In the case that active substances are administered as an injection or drops, syrup or oral drink, the pharmaceutical composition contains 3-(2,2,2-trimethylhydrazinium) propionate and γ-butyrobetaine in the total amount of 0.5 to 40% by weight, and, as pharmaceutically acceptable solvent, distilled water, saline, glucose or buffer solution. In the case the active substances are administered as tablets, caplets, dragee, granules, powders or capsules, they contain 3-(2,2,2-trimethyl-hydrazinium)propionate and γ-butyrobetaine in the total amount of 0.01 to 0.5 g in a tablet, caplet, dragee, capsule or one portion of powder or granule.

In the case the active substances are administered transcutaneously their content in an ointment or plaster makes up 0.5 to 40 % by weight.

In the case the active substances are administered rectally their content in a suppository or microenema accounts for 0.5 to 40 % by weight.

We claim:

1. A pharmaceutical composition for the treatment of cardiovascular diseases, which contains 3-(2,2,2-trimethylhydrazinium)propionate and γ-butyrobetaine as an active system and a pharmaceutically acceptable carrier.

2. The pharmaceutical composition according to claim 1, wherein the ratio of the mentioned substances in the composition is within 1:10.

3. The pharmaceutical composition according to claim 1, which is intended for oral or sublingual administration and is in the form of tablets, with or without coating, capsules, caplets, dragees, granules, powder or solution, which contain 0.01–0.5 g of the active system in every tablet, capsule, dragee, granule or powder dose, or also as a 0.5–40% solution or syrup for oral administration.

4. The pharmaceutical composition according to claim 3, wherein the pharmaceutically acceptable carrier is selected from the group consisting of one or more of the following: stearic acid and its salts, lactose, glucose, saccharose, starch, talc, vegetable oils, polyethylene glycols, microcrystalline cellulose, aerosil, aromatizers, flavoring agents, colorants, ethyl alcohol and water.

5. The pharmaceutical composition according to claim 1, which is intended for parenteral administration and is in a solution for injection, which contains 0.5–40% by weight of the active system and a pharmaceutically acceptable solvent.

6. The pharmaceutical composition according to claim 5, wherein the pharmaceutically acceptable solvent is selected from the group consisting of one or more of the following: distilled water, isotonic solution, buffer solution and glucose solution.

7. The pharmaceutical composition according to claim 1, which is intended for transcutaneous administration of the active system in the form of an ointment, solution or plaster, which contains 0.5–40% by weight of the active system, and a pharmaceutically acceptable carrier.

8. The pharmaceutical composition according to claim 7, wherein the pharmaceutically acceptable carrier is selected from the group consisting of one or more of the following: water, polyethylene glycols 400, 1500 and 4000, vegetable oils, fats, glycerine, preservants, emulgators, stabilizers, porous polymer material, dimethylsulphoxide, alcohol and water.

9. The pharmaceutical composition according to claim 1, which is intended for rectal administration of the active system in the form of suppositories or microenema, which contains 0.5–40% by weight of the active system and a pharmaceutically acceptable carrier.

10. The pharmaceutical composition according to claim 9, wherein the pharmaceutically acceptable carrier is selected from the group consisting of one or more of the following: water, polyethylene glycols 400, 1500 and 4000, vegetable oils, fats, glycerine, preservants, emulgators and stabilizers.

11. A pharmaceutical composition according to claim 2, wherein the ratio of the substances in the composition is within 1:3 to 3:1.

* * * * *